(12) United States Patent
Swenson

(10) Patent No.: US 6,977,323 B1
(45) Date of Patent: Dec. 20, 2005

(54) FOAM-ON-FILM MEDICAL ARTICLES

(75) Inventor: Mary M. Swenson, St. Paul, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/507,108

(22) Filed: Feb. 17, 2000

(51) Int. Cl.[7] .............................................. A61F 13/00
(52) U.S. Cl. ........................................ 602/46; 602/41
(58) Field of Search .................... 602/41–59; 128/888, 128/889; 604/304, 305, 306, 307; 424/443, 424/444, 445, 446, 447

(56) References Cited

U.S. PATENT DOCUMENTS

| | | |
|---|---|---|
| RE24,906 E | 12/1960 | Ulrich |
| 3,975,567 A | 8/1976 | Lock |
| 3,978,855 A | 9/1976 | McRae et al. |
| 4,499,896 A | 2/1985 | Heinecke |
| 4,541,426 A | 9/1985 | Webster |
| 4,561,435 A | 12/1985 | McKnight et al. |
| 4,595,001 A | 6/1986 | Potter et al. |
| 4,598,004 A | 7/1986 | Heinecke |
| 4,609,584 A * | 9/1986 | Cutler et al. ................. 428/156 |
| 4,747,401 A | 5/1988 | Potter et al. |
| 4,798,201 A | 1/1989 | Rawlings et al. |
| 4,833,179 A | 5/1989 | Young et al. |
| 4,871,812 A | 10/1989 | Lucast et al. |
| 4,897,982 A | 2/1990 | Day et al. |
| 4,906,240 A | 3/1990 | Reed et al. |
| 4,917,928 A | 4/1990 | Heinecke |
| RE33,353 E | 9/1990 | Heinecke |
| 5,000,172 A * | 3/1991 | Ward ............................ 602/57 |
| 5,064,653 A | 11/1991 | Sessions et al. |
| 5,065,752 A | 11/1991 | Sessions et al. |
| 5,088,483 A | 2/1992 | Heinecke |
| 5,098,500 A | 3/1992 | Reed et al. |
| 5,160,315 A | 11/1992 | Heinecke et al. |
| 5,183,664 A | 2/1993 | Ansell |
| 5,230,701 A | 7/1993 | Meyer et al. |
| 5,254,301 A | 10/1993 | Sessions et al. |
| 5,271,943 A | 12/1993 | Bogart et al. |
| 5,292,777 A * | 3/1994 | DesMarais et al. ........... 521/64 |
| 5,328,450 A | 7/1994 | Smith et al. |
| 5,409,472 A | 4/1995 | Rawlings et al. |
| 5,512,041 A | 4/1996 | Bogart |
| 5,520,629 A | 5/1996 | Heinecke et al. |
| 5,531,855 A | 7/1996 | Heinecke et al. |
| 5,648,166 A | 7/1997 | Dunshee |
| 5,650,450 A | 7/1997 | Lovette et al. |
| 5,653,699 A | 8/1997 | Reed et al. |
| 5,695,777 A | 12/1997 | Donavan et al. |
| 5,695,855 A * | 12/1997 | Yeo et al. .................... 428/196 |
| 5,738,642 A | 4/1998 | Heinecke et al. |

(Continued)

FOREIGN PATENT DOCUMENTS

DE          2319706 A     11/1973

(Continued)

OTHER PUBLICATIONS

American Society of Testing Materials, "ASTM E-96-80, Standard Test Methods for Water Vapor Transmission of Materials,", *Annual Book of ASTM Standards*, pp. 682-691 (1981).

(Continued)

*Primary Examiner*—Kim M. Lewis
(74) *Attorney, Agent, or Firm*—Nancy M. Lambert

(57) ABSTRACT

The present invention provides a medical article that includes a liquid-impervious, moisture-vapor permeable polymeric film having directly bonded thereto an absorbent, substantially nonswellable foam.

63 Claims, 1 Drawing Sheet

U.S. PATENT DOCUMENTS

| | | | |
|---|---|---|---|
| 5,744,509 | A | 4/1998 | Wilson et al. |
| 5,782,787 | A | 7/1998 | Webster |
| 5,849,325 | A | 12/1998 | Heinecke et al. |
| 5,908,693 | A | 6/1999 | Delgado et al. |
| 5,947,917 | A | 9/1999 | Carte et al. |
| 6,019,996 | A | 2/2000 | Cheong |
| 6,326,410 | B1 | 12/2001 | Cheong ................... 521/67 |

FOREIGN PATENT DOCUMENTS

| | | |
|---|---|---|
| DE | 261126 A | 11/1976 |
| EP | 0 171 268 A2 | 2/1986 |
| EP | 0 171 268 B1 | 1/1989 |
| EP | 0 452 470 | 10/1991 |
| WO | WO 91/06323 | 5/1991 |
| WO | WO 96/10972 | 4/1996 |
| WO | WO 99/19410 | 4/1999 |
| WO | WO 99/27975 | 6/1999 |
| WO | WO 99/28539 | 6/1999 |
| WO | WO 99/28540 | 6/1999 |
| WO | WO 99/47090 A1 | 9/1999 |

OTHER PUBLICATIONS

Wente et al., "Manufacture of Superfine Organic Fibers," Report No. 4364 of the Naval Research Laboratories, Washington, DC, Title page, publication page, abstract, table of contents, and pp. 1-15 (1954).

Wente, "Superfine Thermoplastic Fibers," *Industrial Engineering Chemistry*, 48:1342-1346 (1956).

"Polycril™ Foams," Fulflex Polycril Foams, http://www.fulflex.com/pages/polycrilfoams.html, 2 pages, available on line on or before Dec. 15, 1999.

Lopez, "Enhanced Hydrophilic Polyurethane Prepolymers for Consumer and Industrial Applications," Product Information Brochure from the Dow Chemical Company, Saginaw, Michigan, 8 pgs. (Aug. 2001).

\* cited by examiner

FOAM-ON-FILM MEDICAL ARTICLES

FIELD OF THE INVENTION

The present invention is directed to medical articles, such as wound dressings. Such articles are useful in the treatment of skin lesions, for example.

BACKGROUND OF THE INVENTION

Wound dressings should preferably absorb exudate from lesions without adhering to wound surfaces or floating away from the wound surface. Adhesion problems can occur when the wound has dried out due to the lack of production of exudate. Attempts to remove the dressing will result in disturbance of the newly forming layer of the skin over the wound and hence wound healing is delayed. The problem of dressings that float away from exuding lesions typically occurs when the wound produces particularly large volumes of exudate. Solutions to such problems involve, for example, using a continuous layer that retards the rate of loss of water, thereby preventing adhesion of the dressing to the wound, or providing the dressing with holes so that the exudate can pass through the holes to an absorbent, thereby keeping the dressing in contact with the wound.

It is desirable for effective wound healing to have wound dressings that do not allow the wound to dry out completely and that do not allow exudate to pool. Thus, a breathable wound dressing is desired that can absorb exudate, but not allow the wound to dry out. There are known wound dressings that include foams that attempt to address these problems; however, these dressings can have problems with breathability and with swelling of the foam, which can place pressure on the wound, or alternatively, with poor absorption of exudate.

Thus, many of the known wound dressings are not free of disadvantages since what may be an excellent dressing for one kind of wound will be unsuitable for many other wounds because of the differences in the output of exudate. Thus, additional wound dressings are still needed that are suitable for use on a number of different wound types.

SUMMARY OF THE INVENTION

The present invention provides medical articles (e.g., wound dressings) that include a liquid-impervious, moisture-vapor permeable polymeric film having directly bonded thereto (e.g., directly cast thereon) an absorbent, preferably substantially nonswellable, foam. Preferably, the medical article has a dry moisture vapor transmission rate of less than about 2000 g/m$^2$/24 hours at 38° C. and 20% relative humidity. Preferably, the medical article has a wet moisture vapor transmission rate of at least about 3000 g/m$^2$/24 hours at 38° C. and 20% relative humidity.

Preferably, the foam absorbs greater than 250% by weight aqueous saline solution when immersed in phosphate buffered saline containing 0.9 wt-% NaCl at 37° C. for 30 minutes. Preferably, the foam increases in volume by no greater than about 10% following a 30-minute soaking in phosphate buffered saline at 37° C. Preferably, the absorbent foam is an open cell foam, and can be made from a polyurethane.

Preferably, the liquid-impervious, moisture-vapor permeable polymeric film has a dry moisture vapor transmission rate of at least about 300 g/m$^2$/24 hours at 38° C. and 20% relative humidity. Preferably, the liquid-impervious, moisture-vapor permeable polymeric film has a wet moisture vapor transmission rate of at least about 3000 g/m$^2$/24 hours at 38° C. and 20% relative humidity. If desired, the liquid-impervious, moisture-vapor permeable polymeric film comprises one or more layers. It is preferably a thermoplastic polyurethane.

In another embodiment of the invention, there is provided a medical article that includes a liquid-impervious, moisture-vapor permeable polymeric film having directly bonded thereto an absorbent foam, wherein the article has a dry moisture vapor transmission rate of less than 2000 g/m$^2$/24 hours and a wet moisture vapor transmission rate of at least about 3000 g/m$^2$/24 hours, at 38° C. and 20% relative humidity.

DETAILED DESCRIPTION OF PREFERRED EMBODIMENTS

Figure 1:
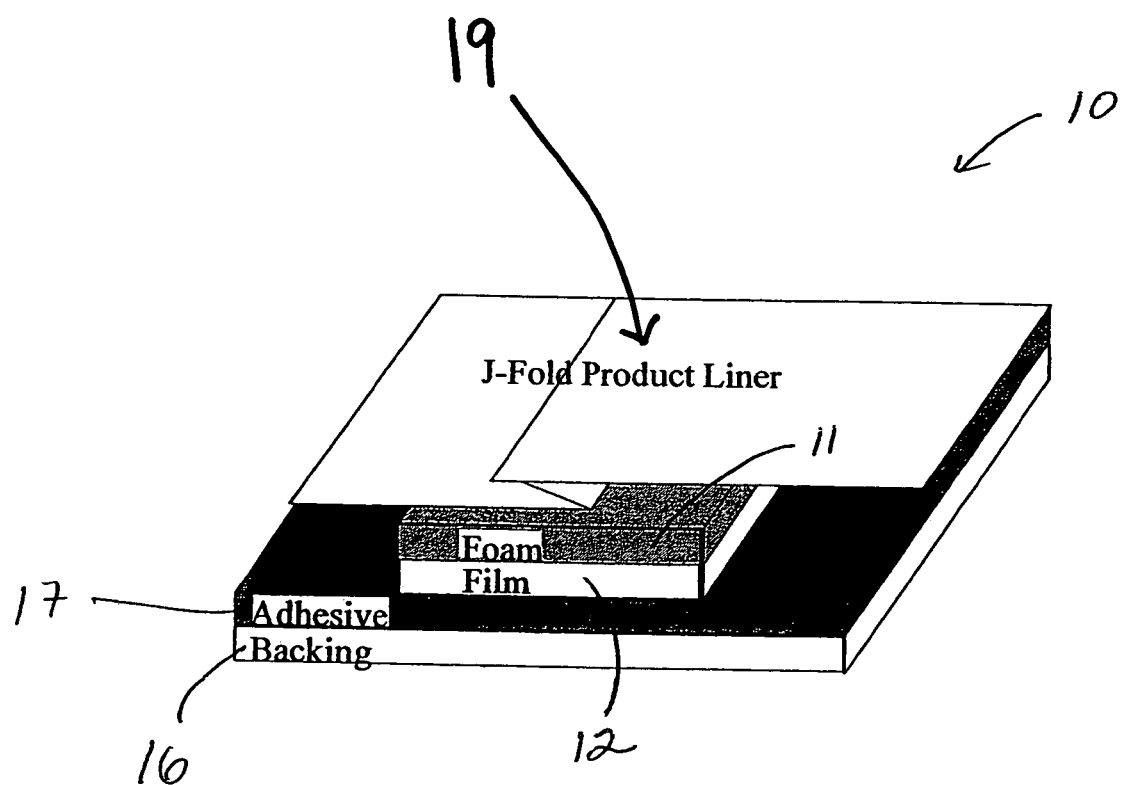
FIG. 1 is representation of a medical dressing that includes an absorbent foam pad directly attached to a liquid-impervious, moisture-vapor permeable film, which is adhesively attached to a backing with an adhesive layer, both of which extend beyond the periphery of the foam/film construction.

The present invention is directed to medical articles, such as wound dressings that are useful in the treatment of skin lesions, for example. Other uses of medical articles of the present invention include, for example, diapers and medical padding such as liposuction padding, hygiene pads, corn and callous pads, toe cushioning pads, ostomy pads, and pads for protecting and cushioning tube sites such as tracheotomy tubes.

Medical articles of the present invention include a liquid-impervious, moisture-vapor permeable polymeric film having directly bonded thereto an absorbent, preferably substantially nonswellable, foam. As used herein, a "foam" refers to a cellular polymeric structure, preferably an open-cell foam; and "directly bonded thereto" means that the foam and film have no intervening adhesive layers, tie layers, or the like. This includes foams directly cast onto films, films directly cast onto foams, as well as thermomechanical bonding such as thermal bonding or ultrasonic welding between the foam and the film. Preferably, the foam is cast directly onto the film using methods well known to one of skill in the art, such as the methods disclosed in U.S. Pat. Nos. 5,064,653 and 5,254,301 (both to Sessions et al.). Whereas the film is typically continuous, the foam may be in discrete islands such that the foam is not coextensive with the film. Preferably, the foam is coextensive with the film.

Medical articles of the present invention are capable of absorbing aqueous saline solution, hence they are capable of absorbing exudate. Preferably, they can absorb greater than 250 weight percent (wt-%), more preferably at least about 500%, and most preferably at least about 800%, by weight aqueous saline solution based on the dry weight of the article. Typically, these values are obtained using a saline absorbency test in which a dry, weighed sample is immersed for 30 minutes at 37° C. in phosphate-buffered saline containing 0.9 wt-% NaCl.

Significantly, medical articles of the present invention typically have a relatively low dry moisture vapor transmission rate (MVTR) and a relatively high wet MVTR. This is important to allow the wound under the dressing to heal under moist conditions without causing the skin surrounding the wound to become macerated.

Herein, dry MVTR is measured by ASTM E-96-80 (American Society of Testing Materials) at 38° C. and 20% relative humidity using an upright cup method and wet MVTR is measured by a similar method, except that the sample jars are inverted so that the water is in direct contact with the test sample. Preferably, medical articles of the present invention have a dry MVTR of less than about 2000 g/m$^2$/24 hours, more preferably less than about 1800 g/m$^2$/24 hours, and most preferably less than about 1500 g/m$^2$/24 hours. Preferably, they also have a wet moisture vapor transmission rate of at least about 3000 g/m$^2$/24 hours, more preferably at least about 5000 g/m$^2$/24 hours, even more preferably at least about 7500 g/m$^2$/24 hours, and most preferably at least about 10,000 g/m$^2$/24 hours.

The liquid-impervious, moisture-vapor permeable polymeric film is a conformable organic polymeric material that preferably retains its structural integrity in a moist environment. Herein, "conformable" films are those that conform to a surface, even upon movement of the surface, as with the surface of a body part. Suitable films have a composition and thickness that allow for the passage of moisture vapor through them. The film aids in the regulation of moisture vapor loss from the wound area beneath the dressing. The film also acts as a barrier to both bacteria and to liquid water or other liquids.

The liquid-impervious, moisture-vapor permeable polymeric films can be of a wide range of thicknesses. Preferably, they are at least about 10 microns (micrometers) thick, and more preferably at least about 12 microns thick. Preferably, they are no greater than about 250 microns, and more preferably no greater than about 75 microns thick. Furthermore, they can include one or more layers tailored to have the desired properties. These layers can be coextruded and/or bonded together with adhesive and/or tie layers, as long as the overall properties of the article, as described herein, are met.

Preferably, suitable films for use in the medical articles of the present invention have differential moisture vapor transmission properties. Preferably, a suitable film has a dry MVTR that is less than the film's wet MVTR. Preferably, suitable films have a dry MVTR of at least about 300 g/m$^2$/24 hours and a wet MVTR of at least about 3000 g/m$^2$/24 hours. The films can be tested using the same methods described above for the article.

Examples of suitable materials for the liquid-impervious, moisture-vapor permeable polymeric films include synthetic organic polymers including, but not limited to: polyurethanes commercially available from B.F. Goodrich, Cleveland, Ohio, under the trade designation ESTANE, including ESTANE 58237 and ESTANE 58245; polyether-amide block copolymers commercially available from Elf Atochem, Philadelphia, Pa., under the trade designation PEBAX, including PEBAX MV1074; polyether-ester block copolymers commercially available from DuPont, Wilmington, Del., under the trade designation HYTREL. The polymeric films can be made of one or more types of monomers (e.g., copolymers) or mixtures (e.g., blends) of polymers. Preferred materials are thermoplastic polymers (e.g., those that soften when exposed to heat and return to their original condition when cooled). A particularly preferred material is a thermoplastic polyurethane.

Medical articles of the present invention include an absorbent foam, preferably a substantially nonswellable foam. In this context, an "absorbent" foam is one that is capable of absorbing saline water, and hence, exudate from a wound. Preferably, suitable foams are those that can absorb greater than 250%, more preferably at least about 500%, and most preferably at least about 800%, by weight aqueous saline solution based on the dry weight of the foam. Typically, these values are obtained using a saline absorbency test in which a dry, weighed sample is immersed for 30 minutes at 37° C. in phosphate-buffered saline containing 0.9 wt-% NaCl.

Preferred foams are also substantially nonswellable. In this context, "substantially nonswellable" means that there is little or no increase in volume of the foam upon absorption of water or saline, and hence, exudate from a wound. Preferably, suitable foams increase in volume by no greater than about 10%, and more preferably by no greater than about 5%, following a 30-minute soaking in phosphate buffered saline, as defined in the test method in the examples below, at 37° C.

Suitable foams can be of a wide range of thicknesses. Preferably, they are at least about 0.5 millimeter, and more preferably at least about 1 millimeter, thick. Preferably, they are no greater than about 80 millimeters, and more preferably no greater than about 30 millimeters, thick. Furthermore, they can include one or more layers tailored to have the desired properties. These layers can be directly bonded to each other or bonded together with adhesive and/or tie layers, as long as the overall properties of the foam and article, as described herein, are met. Optionally, disposed between these layers can be one or more layers of polymeric netting or nonwoven, woven, or knit webs for enhancing the physical integrity of the foam.

Suitably, the foam includes a synthetic polymer that is adapted to form a conformable open cell foam that absorbs the wound exudate. Suitable open cell foams preferably have an average cell size (typically, the longest dimension of a cell, such as the diameter) of at least about 30 microns, more preferably at least about 50 microns, and preferably no greater than about 800 microns, more preferably no greater than about 500 microns, as measured by scanning electron microscopy (SEM) or light microscopy. Such open cell foams when used in dressings of the present invention allow transport of fluid and cellular debris into and within the foam.

Examples of suitable materials for the absorbent, substantially nonswellable foams include synthetic organic polymers including, but not limited to: polyurethanes, carboxylated butadiene-styrene rubbers, polyesters, and polyacrylates. The polymeric foams can be made of one or more types of monomers (e.g., copolymers) or mixtures (e.g., blends) of polymers. Preferred foam materials are polyurethanes. A particularly preferred foam is a polyurethane, available under the trade designation POLYCRIL 400 from Fulflex, Inc., Middleton, R.I.

Although suitable foams may be hydrophilic per se, they are preferably hydrophobic and treated to render them more hydrophilic, for example, with surfactants such as nonionic surfactants, e.g., the oxypropylene-oxyethylene block copolymers available under the trade designation PLURONIC from BASF Wyandotte, Mount Olive, N.J. Use of foams, or surfactants incorporated therein, that possess a hydrophilic surface reduces the tendency for the exudate to coagulate rapidly in the foam. This helps to keep the wound in a moist condition even when production of exudate has ceased from the wound.

Preferably, the film will be coextensive with the foam (as shown in FIG. 1), although in certain embodiments the film will have a greater surface area than the surface area of the foam (i.e., the film will extend beyond the periphery of the foam). For the latter embodiments, the liquid-impervious, moisture-vapor permeable polymeric film can include an adhesive disposed on the surface to which the foam is bonded around the periphery of the foam for adhesion to a surface such as skin. Suitable adhesives for use around the periphery of the foam can be any that are compatible with skin and useful for wound dressings, such as those disclosed in U.S. Pat. Nos. Re. 24,906 (Ulrich) and U.S. Pat. No. 5,849,325 (Heinecke, et al.) (water-based and solvent-based adhesives); U.S. Pat. No. 4,833,179 (Young, et al.) (hot-melt adhesives); U.S. Pat. No. 5,908,693 (Delgado, et al.) (microsphere adhesives); International Publication Nos. WO 99/27975 and 99/28539 (both to Joseph, et al.) (low trauma fibrous adhesives); and, U.S. patent application Ser. Nos. 09/329,514 (Lucast, et al.) PCT/US 99/13,866 (Lucast, et al.), and PCT/US 99/13,865 (Gieselman) (wet-skin adhesives).

The medical articles of the present invention can optionally include a backing, such as a nonwoven, woven, or knit web, bonded to the moisture-vapor permeable polymeric film on a surface opposite the surface to which the foam is bonded. This backing can be bonded directly to the film, as described above for bonding of the foam to the film (e.g., cast or thermomechanical bonding), or bonded to the film using an adhesive layer, for example. Suitable adhesives for bonding the film surface opposite the foam to the backing can be any of those useful for wound dressings, such as those referenced in the above paragraph. Preferably, the adhesive is a fibrous adhesive as disclosed in International Publication Nos. WO 99/27975 and 99/28539.

The medical articles of the present invention can optionally include a wound-contacting material bonded to the exposed surface of the foam (i.e., the surface opposite the surface to which the film is bonded). Examples of such wound-contacting materials include polymeric netting and porous (e.g., perforated) films, or other conventional materials that prevent the dressing from sticking to the wound. This wound-contacting layer can be bonded directly to the foam, as described above for bonding of the foam to the film (e.g., cast or thermomechanical bonding), or bonded to the foam using an adhesive layer, for example.

Referring to the figure, a preferred embodiment is specifically shown. FIG. 1 is a representation of a medical dressing 10 that includes a foam pad 11 directly attached to a film 12. This foam/film construction is adhesively attached to a backing 16, such as a nonwoven web, with an adhesive layer 17, both of which extend beyond the periphery of the foam/film construction. Also shown is a liner 19, such as a J-fold liner.

The medical articles of the invention can include graphics printed on the liquid-impervious, moisture-vapor permeable polymeric film. Suitable inks and methods of applying such graphics are disclosed in International Publication No. WO 99/19410 (Dunshee, et al.). Such graphics can be placed on either major surface of the film. If placed on the surface of the film that is in contact with the foam, there is preferably no greater than about 10% of the surface area covered by the ink.

The medical articles of the invention can contain a topically active medicament, such as an antibacterial agent. Preferably the antibacterial agent is a broad-spectrum antibacterial agent such as a silver salt, a sulphadiazine, an acceptable iodine source such as povidone iodine (also called polyvinyl pyrrolidone-iodine or PVP/I), chlorhexidine salts such as the gluconate, acetate, hydrochloride or the like salts or quaternary antibacterial agents such as benzalkonium chloride. Favored antibacterial agents include the salts of chlorhexidine. Preferably the medicament is present in the foam layer.

Typically, the medical articles of this invention are sterile and are provided sealed within a bacteria-proof package. The medical article may be rendered sterile by any suitable sterilization means, for example by gamma irradiation, steam sterilization, or ethylene oxide.

One process of manufacturing the dressings of the present invention is by casting the foam onto a film using a method such as disclosed in U.S. Pat. Nos. 5,064,653 and 5,254,301 (both to sessions et al.). The films can be made from an appropriate thermoplastic resin by conventional extrusion processes, for example, as described in U.S. Pat. No. 4,499,896 (Heinecke). The film is generally supported on a standard release liner during the foam-casting operation. Preferably, the release liner is easily separated from the film following casting of the foam.

Objects and advantages of this invention are further illustrated by the following examples, but the particular materials and amounts thereof recited in these examples, as well as other conditions and details, should not be construed to unduly limit this invention. Unless otherwise indicated, all parts and percentages are by weight.

EXAMPLES

Test Protocols

Saline Water Absorbency

Evaluation of saline water absorbency was measured using the following test procedure. A 5.1-cm×5.1-cm sample was immersed in phosphate-buffered saline (Sigma-Aldrich Chemical Co., Milwaukee, Wis.; dry powder blend dissolved in water to 0.9% NaCl) for thirty minutes at 37° C., removed, allowed to drip freely for thirty seconds, and re-weighed. The sample percent absorbency was then calculated using the formula: Absorbency (%)=(Wet Sample Weight−Dry Sample Weight)×100÷Dry Sample Weight. Results reported are the average of at least three replications.

Swell

Evaluation of swell was measured using the following test procedure. The width (W), length (L), and thickness (T) of an approximate 5.1-cm×5.1-cm dry sample were accurately measured. The sample was immersed in phosphate-buffered saline (as described above) for thirty minutes at 37° C., removed, allowed to drip freely for thirty seconds, and all three dimensions of the sample were immediately re-measured. The sample percent swell was then calculated using the formula: Swell (%)=[W×L×T(Wet)−W×L×T(Dry)]×100÷W×L×T(Dry). Results reported are the average of at least three replications.

Moisture Vapor Transmission Rate (Standard "Dry" Method)

The "dry" moisture vapor transmission rate (MVTR) was measured according to ASTM E-96-80 using a modified Payne cup method. Specifically, a sample (3.5-cm diameter) was placed between adhesive-containing surfaces of two foil adhesive rings, each having a 2.54-cm diameter hole. The holes of each ring were carefully aligned. Finger pressure was used to form a foil/sample/foil assembly that was flat, wrinkle-free, and had no void areas in the exposed sample.

A 120-ml glass jar was filled to the halfway level with deionized water. The jar was fitted with a screw-on cap having a 3.8-cm diameter hole in the center thereof and with a 4.45-cm diameter rubber washer having a 2.84-cm diameter hole in its center. The rubber washer was placed on the lip of the jar and the foil/sample assembly was placed on the rubber washer. The lid was then screwed loosely on the jar.

The assembly was placed in a chamber at 38° C. and 20% relative humidity for four hours. At the end of four hours, the cap was tightened inside the chamber so that the sample was level with the cap (no bulging) and the rubber washer was in proper seating position.

The foil/sample assembly was then removed from the chamber and weighed immediately to the nearest 0.01 gram (initial weight $W_1$). The assembly was then returned to the chamber for at least 18 hours, after which it was removed and weighed immediately to the nearest 0.01 gram (final weight $W_2$). The MVTR in grams of water vapor transmitted per square meter of sample area in 24 hours was calculated according to the following formula (where "$T_1$" refers to exposure time in hours):

"Dry" $MVTR=(W_1-W_2) (4.74\times10^4)\div T_1$

Three measurements of each sample were made, and the average value taken. The MVTR values are reported as g/m²/24 hrs.

Moisture Vapor Transmission Rate (Inverted "Wet" Method)

The inverted "wet" MVTR was measured using the following test procedure. After obtaining the final "dry" weight ($W_2$) as described for the "dry" MVTR procedure, the assembly was returned to the chamber (38° C. and 20% relative humidity) for at least 18 additional hours with the sample jars inverted so that the deionized water was in direct contact with the test sample. The sample was then removed from the chamber and weighed to the nearest 0.01 gram (final "wet" weight, W3). The inverted "wet" MVTR in grams of water vapor transmitted per square meter of sample area in 24 hours was calculated according to the following formula (where "$T_2$" refers to exposure time in hours):

Inverted "Wet" $MVTR=(W_2-W_3)(4.74\times10^4)\div T_2$

Three measurements of each sample were made, and the average value taken. The Inverted "Wet" MVTR values are reported as g/m²/24 hrs.

Adhesive Starting Material

Adhesive 1 (Blown Micro Fiber (BMF)-Acrylate-PSA Web)

A porous polyacrylate-based BMF-PSA web was prepared using a melt blowing process similar to that described, for example, in Wente, Van A., "Superfine Thermoplastic Fibers," in *Industrial Engineering Chemistry*, Vol. 48, pages 1342 et seq (1956) or in Report No. 4364 of the Naval Research Laboratories, published May 25, 1954, entitled "Manufacture of Superfine Organic Fibers" by Wente, Van A.; Boone, C. D.; and Fluharty, E. L., except that the BMF apparatus utilized a single extruder which fed its extrudate to a gear pump that controlled the polymer melt flow. The gear pump fed a feedblock assembly that was connected to a melt-blowing die having circular smooth surface orifices (10/cm) with a 5:1 length to diameter ratio. The primary air was maintained at 220° C. and 241 KPa with a 0.076-cm gap width to produce a uniform web. The feedblock assembly was fed by a polymer melt stream (240° C.) comprised of isooctyl acrylate/acrylic acid/styrene macromer (IOA/AA/Sty, 92/4/4 ratio, Inherent Viscosity ~0.65 as measured by conventional means using a Cannon-Fenski #50 viscometer in a water bath controlled at 25° C. to measure the flow time of 10 ml of a polymer solution (0.2 g per deciliter polymer in ethyl acetate) PSA, prepared as described in Example 2 of U.S. Pat. No. 5,648,166 ("Dunshee"). Both the die and feedblock assembly were maintained at 220° C., and the die was operated at a rate of 178 g/hr/cm die width. The BMF-PSA web was collected on a double-coated silicone release paper (DCP-Lohja, Westchester, Ill.) which passed around a rotating drum collector at a collector to die distance of 17.8 cm. The resulting BMF-PSA web, comprising PSA microfibers having an average diameter of less than about 25 microns (as determined using a scanning electron microscope), had a basis weight of about 60 g/m².

Example 1

Foam/Film Composite

Polyurethane foam (available under the trade designation POLYCRIL 400, Fulflex, Inc., Middleton, R.I.) was cast at a thickness of 6.4 mm onto a sheet of 1.0-mil (25-microns) thick polyurethane film (extruded from polyurethane resin available under the trade designation ESTANE 58237 resin from B. F. Goodrich, Cleveland, Ohio as described in U.S. Pat. No. 4,499,896 ("Heinecke") that was supported on standard MUL carrier paper (Schoeller Technical Papers, Pulaski, N.Y.). The film was observed to be very tightly bonded to the foam and it was not possible to peel the film layer from the foam layer without causing damage to the foam. The carrier paper could easily be stripped away from the film. The resulting foam-film composite was cut into samples that were later used in absorbency, swell, and MVTR evaluations. Evaluation results are reported in Table 1.

Examples 2a–2c

Foam/Film Composites with Graphics

A foam-film composite was prepared according to Example 1, except that, prior to casting the foam, the polyurethane film was printed (on the side to be foam-cast) with graphics as generally described in U.S. Patent Application "Abrasion-Resistant Ink Compositions and Methods of Use", Ser. No. 08/949,903 (except that the printed graphics did not include primer and low adhesion backside coatings). The polyurethane foam was cast at thicknesses of 3.0 mm (Example 2a), 6.4 mm (Example 2b), and 15.7 mm (Example 2c). For all resulting samples, the film was observed to be very tightly bonded to the foam and it was not possible to peel the film layer from the foam layer without causing damage to the foam. The carrier paper could easily be stripped away from the film. The resulting foam-film composites were cut into samples that were later used in absorbency, swell, and MVTR evaluations. Evaluation results are reported in Table 1.

Examples 3–4

Foam/Film Composites

Foam-film composites were prepared according to Example 1, except that different resins were used in place of ESTANE 58237 to prepare the extruded film layers. The POLYCRIL 400 foam was cast onto films made from ESTANE 58245 polyurethane (B. F. Goodrich) and PEBAX MV1074 (polyether-amide block copolymer, Elf Altochem North America, Philadelphia, Pa.) to provide foam-film composites designated Example 3 and Example 4, respectively. In each case, the film was observed to be very tightly bonded to the foam and it was not possible to peel the film layer from the foam layer without causing damage to the foam. Also, in each case, the carrier paper could easily be stripped away from the film. The resulting foam-film composites were cut into samples that were later used in absorbency, swell, and MVTR evaluations. Evaluation results are reported in Table 1.

Example 5

Foam Materials

The following commercial foam materials were cut into samples and evaluated for absorbency and swell: foams available under the trade designations HYDRASORB (HY-POL) from W.R. Grace & Co., Columbia, Md., EPI-LOCK from Calgon/Vestal Laboratories, St. Louis, Mo., LYO-FOAM from ConvaTec, Skillman, N.J., and POLYCRIL 400 from Fulflex, Inc. Results are reported in Table 2.

Examples 6–9

Foam/Film Composites

Foam-film composites were prepared according to Example 1, except that different resins were used in place of ESTANE 58237 to prepare the extruded film layers. The POLYCRIL 400 foam was cast onto films made from polyurethane available under the trade designation ESTANE 58309 from B. F. Goodrich on a silicone-coated paper carrier (77 pound CIS No. 87680-865 Medical Liner Base, Glatfelter, Spring Grove, Pa.), PE-44 MORTHANE polyurethane (Morton International, Inc., Seabrook, N.H.) on a paper carrier (2-78BLSCK-164 & 28, DCP-Lohja, Westchester, Ill.), HYTREL 8171 polyester (Dupont, Wilmington, Del.) on standard MUL paper carrier, and HYTREL 8206 polyester (Dupont) on standard MUL paper carrier to provide foam-film composites designated as Example 6, Example 7, Example 8, and Example 9, respectively. The film, in each case, was observed to be very tightly bonded to the foam and it was not possible to peel the film layer from the foam layer without causing damage to the foam. Also, in each case, the carrier paper was bonded tightly to the film and could not easily be stripped away from the film without causing some damage to the foam-film composite. No further evaluations or testing were made on these samples.

Example 10

Foam/Film Pad//Adhesive//Nonwoven Dressing

The polyacrylate BMF-PSA web (Adhesive 1, including release liner) was laminated to a melt blown polyurethane nonwoven web (basis weight 100 g/m$^2$; prepared from MORTHANE PS-440 (Morton International, Inc.) as described in Example 1 of U.S. Pat. No. 5,230,701 ("Meyer et al."), using a laboratory laminator having two steel rollers with the bottom roller temperature set at 93° C. and the top roller temperature set at 113° C. The gap width between rollers was 0.2 mm, the nip pressure was 620 KPa, and the line speed was 122 cm/min. The release liner was removed from the resulting adhesive/nonwoven laminate and an island dressing was constructed by placing a 7.6-cm×7.6-cm pad of the foam/film composite of Example 1 in the center of a 10-cm×10-cm sample of the adhesive/nonwoven laminate (film layer in direct contact with the adhesive layer) and applying light finger pressure to the pad to ensure good adhesion to the nonwoven backing. A 10-cm×10-cm standard J-fold silicone product release liner (DCP-Lohja, Westchester, Ill.) was placed over the foam layer and pressed against the adhesive layer to form the completed dressing. The resulting composite dressing was cut into samples that were later used in absorbency, swell, and MVTR evaluations. Evaluation results are reported in Table 1.

Example 11

Foam/Film Pad//Adhesive//Nonwoven Dressing

A composite dressing was prepared as described in Example 10, except that a hydroentangled, spunbond, 100% polyester web (SONTARA 8010, Dupont, Wilmington, Del.) was used in place of the polyurethane nonwoven web. The resulting composite dressing was cut into samples that were later used in absorbency, swell, and MVTR evaluations. Evaluation results are reported in Table 1.

Comparative Example A

Foam/Film Composite

A foam-film composite was prepared according to Example 1, except that POLYCRIL 300 foam (Fulflex, Inc.) was used in place of the POLYCRIL 400 foam. The film was observed to be very tightly bonded to the foam and it was not possible to peel the film layer from the foam layer without causing damage to the foam. Also, the carrier paper could easily be stripped away from the film. The resulting foam-film composite was cut into samples that were later used in absorbency, swell, and MVTR evaluations. Evaluation results are reported in Table 1.

Test Data

Composite dressings from Examples 1, 2a–2c, 3, 4, 10, 11, and Comparative Example A were cut into appropriate sample sizes and evaluated for saline water absorbency, swell, "Dry" MVTR, and "Wet" MVTR. The results are shown in Table 1 along with results for two commercial non-adhesive foam/film dressings, ALLEVYN dressing (Smith & Nephew, York, England) and POLYMEM (Ferris Mfg. Co., Burr Ridge, Ill.). Additionally, foam samples as listed in Example 5 were evaluated for saline water absorbency and swell with results shown in Table 2.

TABLE 1

| Example | Buffered Saline Absorbency (%) | Swell (%) | Dry MVTR (g/m$^2$/24 hr) | Wet MVTR (g/m$^2$/24 hr) |
| --- | --- | --- | --- | --- |
| 1 | 810* | 8 | 1492* | 5303* |
| 2a | 575 | −5 | 1780 | 8889 |
| 2b | 981 | 1 | 1740 | 12,060 |
| 2c | 1201 | 7 | 1497 | 10,984 |
| 3 | 970 | 4 | 2520 | 15,830 |
| 4 | 900 | 0 | 2810 | 16,280 |
| Comparative A | 1150 | 50 | 2300 | 26,150 |
| 10 | 690 | 8 | 940 | 4550 |
| 11 | 700 | 8 | 1905 | 9900 |
| ALLEVYN | 600–800 | 40 | 1000 | 1600–2000 |
| POLYMEM | 500 | 60 | 700 | 900 |

*Average for eight consecutive runs

TABLE 2

| Foam Sample (Example 5) | Buffered Saline Absorbency (%) | Swell (%) |
| --- | --- | --- |
| HYDRASORB | 1367 | 89 |
| EPI-LOCK | 1434 | 90 |
| LYOFOAM | 218 | 11 |
| POLYCRIL 400 | 1089 | 8 |

As shown in Table 1, composite dressings of the present invention (Examples 1–4 and 10–11) all had swell values less than 10%. In contrast, Comparative Example A and the commercial dressings had swell values in the range of 40–60%. Additionally, the composite dressings of the present invention had dry MVTR values less than 3000 g/m$^2$/24 hours, and in some cases less than 2000 g/m$^2$/24 hours; and had wet MVTR values of greater than 4500 g/m$^2$/24 hours. The data from Table 2 show that among the four foam samples evaluated, only POLYCRIL 400 had low swell (8%) coupled with high absorbency (1089%).

All patents, patent applications and publications are incorporated by reference herein as though individually incorporated by reference. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A medical article comprising a liquid-impervious, moisture-vapor permeable polymeric film having directly bonded thereto an absorbent, substantially nonswellable foam comprising a hydrophobic polymer, wherein the article has a dry moisture vapor transmission rate of less than about 2000 g/m$^2$/24 hours at 38° C. and 20% relative humidity.

2. The medical article of claim 1 which has a wet moisture vapor transmission rate of at least about 3000 g/m$^2$/24 hours at 38° C. and 20% relative humidity.

3. The medical article of claim 2 which has a wet moisture vapor transmission rate of at least about 5000 g/m$^2$/24 hours at 38° C. and 20% relative humidity.

4. The medical article of claim 1 which has a dry moisture vapor transmission rate of less than about 1800 g/m$^2$/24 hours at 38° C. and 20% relative humidity.

5. The medical article of claim 4 which has a dry moisture vapor transmission rate of less than about 1500 g/m$^2$/24 hours at 38° C. and 20% relative humidity.

6. The medical article of claim 1 wherein the foam absorbs greater than 250% by weight aqueous saline solution when immersed in phosphate buffered saline containing 0.9 wt-% NaCl at 37° C. for 30 minutes.

7. The medical article of claim 1 wherein the liquid-impervious, moisture-vapor permeable polymeric film has a dry moisture vapor transmission rate of at least about 300 g/m$^2$/24 hours at 38° C. and 20% relative humidity.

8. The medical article of claim 7 wherein the liquid-impervious, moisture-vapor permeable polymeric film has a wet moisture vapor transmission rate of at least about 3000 g/m$^2$/24 hours at 38° C. and 20% relative humidity.

9. The medical article of claim 1 wherein the liquid-impervious, moisture-vapor permeable polymeric film comprises one or more layers.

10. The medical article of claim 1 wherein the liquid-impervious, moisture-vapor permeable polymeric film is a thermoplastic polyurethane.

11. The medical article of claim 1 wherein the liquid-impervious, moisture-vapor permeable polymeric film has a thickness of about 10 microns to about 250 microns.

12. The medical article of claim 1 wherein the substantially nonswellable foam increases in volume by no greater than about 10% following a 30-minute soaking in phosphate buffered saline at 37° C.

13. The medical article of claim 12 wherein the substantially nonswellable foam increases in volume by no greater than about 5% following a 30-minute soaking in phosphate buffered saline at 37° C.

14. The medical article of claim 1 wherein the substantially nonswellable foam is an open cell foam.

15. The medical article of claim 14 wherein the substantially nonswellable foam comprises a hydrophobic polyurethane.

16. The medical article of claim 1 wherein the liquid-impervious, moisture-vapor permeable polymeric film includes graphics printed thereon.

17. The medical article of claim 1 wherein the liquid-impervious, moisture-vapor permeable polymeric film extends beyond a periphery of the foam.

18. The medical article of claim 17 wherein the liquid-impervious, moisture-vapor permeable polymeric film includes an adhesive disposed on the surface to which the foam is bonded around the periphery of the foam.

19. The medical article of claim 1 wherein a nonwoven, woven, or knit web is bonded to the moisture-vapor polymeric film on a surface opposite the surface to which the foam is bonded.

20. The medical article of claim 19 wherein the moisture-vapor polymeric film is bonded to the nonwoven, woven, or knit web with a fibrous adhesive.

21. The medical article of claim 1 wherein the foam is cast directly on the film.

22. The medical article of claim 1 which is a wound dressing.

23. The medical article of claim 1 wherein the foam comprises a hydrophobic polymer treated with a surfactant.

24. A medical article comprising a liquid-impervious, moisture-vapor permeable polymeric film having directly bonded thereto an absorbent, substantially nonswellable foam comprising a hydrophobic polymer, wherein the article has a wet moisture vapor transmission rate of at least about 3000 g/m$^2$/24 hours, at 38° C. and 20% relative humidity.

25. The medical article of claim 24 which has a wet moisture vapor transmission rate of at least about 5000 g/m$^2$/24 hours at 38° C. and 20% relative humidity.

26. The medical article of claim 24 which has a dry moisture vapor transmission rate of less than about 1800 $\mu$m$^2$/24 hours at 38° C. and 20% relative humidity.

27. The medical article of claim 24 wherein the foam absorbs greater than 250% by weight aqueous saline solution when immersed in buffered saline containing 0.9 wt-% NaCl at 37° C. for 30 minutes.

28. The medical article of claim 24 wherein the liquid-impervious, moisture-vapor permeable polymeric film comprises one or more layers.

29. The medical article of claim 24 wherein the substantially nonswellable foam increases in volume by no greater than about 10% following a 30-minute soaking in phosphate buffered saline at 37° C.

30. The medical article of claim 24 wherein the substantially nonswellable foam is an open cell foam.

31. The medical article of claim 24 wherein the liquid-impervious, moisture-vapor permeable polymeric film extends beyond a periphery of the foam.

32. The medical article of claim 31 wherein the liquid-impervious, moisture-vapor permeable polymeric film includes an adhesive disposed on the surface to which the foam is bonded around the periphery of the foam.

33. The medical article of claim 24 wherein a nonwoven, woven, or knit web is bonded to the moisture-vapor, polymeric film on a surface opposite the surface to which the foam is bonded.

34. The medical article of claim 24 wherein the foam is cast directly on the film.

35. The medical article of claim 24 which is a wound dressing.

36. The medical article of claim 24 wherein the foam comprises a hydrophobic polymer treated with a surfactant.

37. A wound dressing comprising a polyurethane film having directly bonded thereto an absorbent, substantially nonswellable foam comprising a hydrophobic polyurethane, wherein:
the polyurethane film has a dry moisture vapor transmission rate of at least about 300 g/m$^2$/24 hours at 38° C. and 20% relative humidity and a wet moisture vapor transmission rate of at least about 3000 g/m$^2$/24 hours at 38° C. and 20% relative humidity; and
the foam increases in volume by no greater than about 10% following a 30-minute soaking in phosphate buffered saline at 37° C.

38. A medical article comprising a liquid-impervious, moisture-vapor permeable polymeric film having directly bonded thereto an absorbent, substantially nonswellable foam comprising a hydrophobic polymer, wherein the foam absorbs greater than 250% by weight aqueous saline solution when immersed in phosphate buffered saline containing 0.9 wt-% NaCl at 37° C. for 30 minutes.

39. The medical article of claim 38 which has a dry moisture vapor transmission rate of less than about 2000 g/m$^2$/24 hours at 38° C. and 20% relative humidity.

40. The medical article of claim 38 which has a wet moisture vapor transmission rate of at least about 3000 g/m$^2$/24 hours at 38° C. and 20% relative humidity.

41. The medical article of claim 38 wherein the liquid-impervious, moisture-vapor permeable polymeric film has a dry moisture vapor transmission rate of at least about 300 g/m$^2$/24 hours at 38° C. and 20% relative humidity.

42. The medical article of claim 41 wherein the liquid-impervious, moisture-vapor permeable polymeric film has a wet moisture vapor transmission rate of at least about 3000 g/m$^2$/24 hours at 38° C. and 20% relative humidity.

43. The medical article of claim 38 wherein the liquid-impervious, moisture-vapor permeable polymeric film is a thermoplastic polyurethane.

44. The medical article of claim 38 wherein the liquid-impervious, moisture-vapor permeable polymeric film has a thickness of about 10 microns to about 250 microns.

45. The medical article of claim 38 wherein the substantially nonswellable foam increases in volume by no greater than about 10% following a 30-minute soaking in phosphate buffered saline at 37° C.

46. The medical article of claim 38 wherein the substantially nonswellable foam is an open cell foam.

47. The medical article of claim 46 wherein the substantially nonswellable foam comprises a hydrophobic polyurethane.

48. The medical article of claim 38 wherein a nonwoven, woven, or knit web is bonded to the moisture-vapor polymeric film on a surface opposite the surface to which the foam is bonded.

49. The medical article of claim 38 wherein the foam is cast directly on the film.

50. The medical article of claim 38 which is a wound dressing.

51. A medical article comprising a liquid-impervious, moisture-vapor permeable polymeric film having directly bonded thereto an absorbent, substantially nonswellable foam comprising a hydrophobic polymer, wherein the substantially nonswellable foam increases in volume by no greater than about 10% following a 30-minute soaking in phosphate buffered saline at 37° C.

52. The medical article of claim 51 which has a dry moisture vapor transmission rate of less than about 2000 g/m$^2$/24 hours at 38° C. and 20% relative humidity.

53. The medical article of claim 51 which has a wet moisture vapor transmission rate of at least about 3000 g/m$^2$/24 hours at 38° C. and 20% relative humidity.

54. The medical article of claim 51 wherein the foam absorbs greater than 250% by weight aqueous saline solution when immersed in phosphate buffered saline containing 0.9 wt-% NaCl at 37° C. for 30 minutes.

55. The medical article of claim 51 wherein the liquid-impervious, moisture vapor permeable polymeric film has a dry moisture vapor transmission rate of at least about 300 g/m$^2$/24 hours at 38° C. and 20% relative humidity.

56. The medical article of claim 51 wherein the liquid-impervious, moisture-vapor permeable polymeric film is a thermoplastic polyurethane.

57. The medical article of claim 51 wherein the liquid-impervious, moisture-vapor permeable polymeric film has a thickness of about 10 microns to about 250 microns.

58. The medical article of claim 51 wherein the substantially nonswellable foam increases in volume by no greater than about 5% following a 30-minute soaking in phosphate buffered saline at 37° C.

59. The medical article of claim 51 wherein the substantially nonswellable foam is an open cell foam.

60. The medical article of claim 59 wherein the substantially nonswellable foam comprises a hydrophobic polyurethane.

61. The medical article of claim 51 wherein a nonwoven, woven, or knit web is bonded to the moisture-vapor polymeric film on a surface opposite the surface to which the foam is bonded.

62. The medical article of claim 51 wherein the foam is cast directly on the film.

63. The medical article of claim 51 which is a wound dressing.

* * * * *

UNITED STATES PATENT AND TRADEMARK OFFICE
CERTIFICATE OF CORRECTION

PATENT NO. : 6,977,323 B1
APPLICATION NO. : 09/507108
DATED : December 20, 2005
INVENTOR(S) : Mary M. Swenson Page 1 of 1

It is certified that error appears in the above-identified patent and that said Letters Patent is hereby corrected as shown below:

Title Page
Item [56], References Cited, OTHER PUBLICATIONS, after "Materials,"" delete ",".

Column 6
Line 9, after "(both to" delete "sessions" and insert -- Sessions--, therefore.

Column 7
Line 36, after "($4.74 \times 10^4$)" delete "+" and insert -- ÷ --, therefore.
Line 67, delete "("Dunshee")" and insert -- (Dunshee) --, therefore.

Column 12
Line 51, delete "$\mu m^2$" and insert -- $g/m^2$ --, therefore.

Column 14
Line 31, after "moisture" insert -- - --.

Signed and Sealed this

Thirty-first Day of July, 2007

JON W. DUDAS
*Director of the United States Patent and Trademark Office*